United States Patent [19]

Ross et al.

[11] 4,216,219

[45] Aug. 5, 1980

[54] DIMERIC OXAZOLE DERIVATIVES

[75] Inventors: William J. Ross, Lightwater; Alec Todd, Wokingham, both of England

[73] Assignee: Lilly Industries Limited, London, England

[21] Appl. No.: 10,185

[22] Filed: Feb. 7, 1979

[30] Foreign Application Priority Data

Feb. 14, 1978 [GB] United Kingdom ............... 5747/78

[51] Int. Cl.² ..................... A61K 31/42; C07D 263/48
[52] U.S. Cl. ................................... 424/272; 548/233
[58] Field of Search .................... 260/307 R; 548/233; 424/272

Primary Examiner—José Tovar

Attorney, Agent, or Firm—Charles W. Ashbrook; Arthur R. Whale

[57] ABSTRACT

Novel compounds are described of the formula

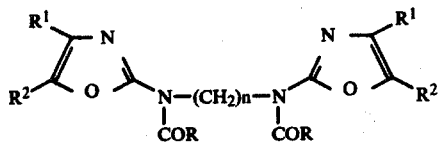

where R is $C_{2-6}$ alkyl, $R^1$ and $R^2$ are hydrogen or $C_{1-4}$ alkyl and n is 3 to 6. The compounds are useful in the prophylactic treatment of immediate hypersensitivity diseases including asthma.

12 Claims, No Drawings

DIMERIC OXAZOLE DERIVATIVES

This invention relates to certain novel oxazole derivatives which possess pharmacological activity and also includes within its ambit processes for preparing the compounds of the invention, as well as pharmaceutical compositions containing the pharmacologically active compounds and methods of treatment of animals, including humans, comprising administering thereto an effective dose of the compound or compounds or of pharmaceutical compositions comprising the active compound or compounds.

According to the present invention there is provided a compound of the formula:

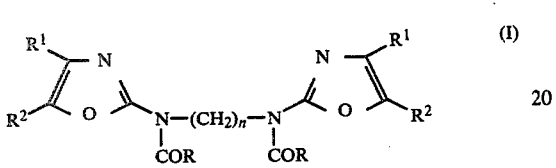

where R is $C_{2-6}$ alkyl, $R^1$ and $R^2$ are hydrogen or $C_{1-4}$ alkyl and n is 3 to 6.

Preferably, $R^1$ is $C_{1-3}$ alkyl, for instance methyl, when $R^2$ is hydrogen.

In one aspect of the invention there is provided a method of preparing compounds of formula (I) which comprises reacting two moles of an acylamino derivative of formula (II):

where R, $R^1$ and $R^2$ are as previously defined, with one mole of a compound of formula:

where n is as previously defined and X is a leaving radical such as bromine or tosyl.

The acylamino derivatives of formula (II) are known compounds, their preparation being described in for example United Kingdom Patent Specification No. 1,264,258.

The reaction can be accomplished in the presence of a base such as potassium carbonate, sodium carbonate or sodium hydride. Any suitable polar solvent such as dimethylformamide, tetrahydrofuran or diethyl ether can be used.

At temperatures between 40° and 100° C. substantial amounts of the reaction product have been formed after 3 hours.

In a second aspect of the invention there is provided a method of preparing a compound of formula (I) which comprises acylating an amino derivative of formula (III):

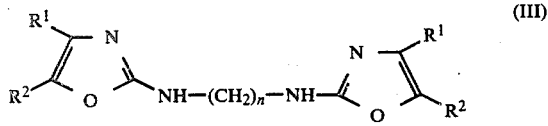

where $R^1$, $R^2$ and n are as previously defined.

Any of the standard acylating agents conventionally used and known to those skilled in the art may be used and it would be otiose to list them here. Similarly, the reaction conditions used to effect acylation reactions are very well known.

The compounds of formula (III) may be prepared from known starting materials by the following reaction scheme:

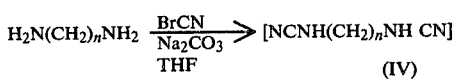

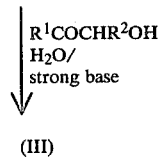

The reaction of the alkylenediamine with the bromocyanogen reagent is preferably carried out in an ethereal solvent such as tetrahydrofuran at a temperature of from $-10°$ C. to $-25°$ C. Some of the cyanamides of formula (IV) thus formed are known compounds (see, for instance, *J. Org. Chem.* 26, 4122 (1961)). Conversion of the cyanamide to the amine of formula (III) with the hydroxy ketone may be effected using a strong base such as caustic soda in aqueous solution.

Compounds of formula (I) have been shown to be useful in the prophylactic treatment of immediate hypersensitivity diseases including asthma. The compounds have low toxicity.

The compounds or compositions of the present invention may be administered by various routes and for this purpose may be formulated in a variety of forms. Thus the compounds or compositions may be administered by the oral or rectal routes, topically, parenterally, e.g. by the injection and by continuous or discontinuous intra-arterial infusion, in the form of, for example, tablets, lozenges, sub-lingual tablets, sachets, cachets, elixirs, suspensions, aerosols, ointments for example containing from 1 to 10% by weight of the active compound in a suitable base, soft and hard gelatin capsules, suppositories, injection solutions and suspensions in physiologically acceptable media, and sterile packaged powders absorbed onto a support material for injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). In human chemotherapy dosages of from 1 to 30 mg/kg per day, preferably 2 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore, the above preferred dosage ranges are not intended to limit the scope of the present invention in any way.

According to a further aspect of the invention there is provided a pharmaceutical formulation which comprises a compound of formula (I) associated with a pharmaceutically acceptable carrier therefor.

The carrier may be any solid, semi-solid or liquid material, which serves as a vehicle, excipient or medium for the active therapeutic substance. Some examples of the diluents or carriers which may be employed in the pharmaceutical formulations of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The invention will now be illustrated with reference to the following non-limitative Examples.

EXAMPLE 1

N,N$^1$-1,4-butanediylbis[2-methyl-N-(4-methyl-2-oxazolyl)propanamide]

A stirred mixture of 2-methyl-N-(4-methyl-2-oxazolyl)-propanamide (8.4 g, 0.05 mol), potassium carbonate (13.8 g, 0.10 mol) and 1,4-dibromobutane (3.0 ml, 0.025 mol) in dry dimethylformamide (50 ml) was heated at 70° C. for 40 minutes. The mixture was cooled, poured onto ice and extracted with ether (3×100 ml). The extract was washed with dilute HCl, dried and evaporated to give the title compound as a white solid which was recrystallised from ether-petroleum spirit 40°-60° C.) yield 4.8 g, m.p. 94°-96° C.

EXAMPLES 2 TO 4

The following compounds were prepared by similar methods to that of Example 1:

N,N$^1$-1,3-propanediylbis[2-methyl-N-(4-methyl-2-oxazolyl)propanamide] b.p. 160° C./0.05 mm.

N,N$^1$-1,5-pentanediylbis[2-methyl-N-(4-methyl-2-oxazolyl)propanamide] b.p. 190° C./0.2 mm.

N,N$^1$-1,4-butanediylbis[N-(4-methyl-2-oxazolyl)-pentanamide] m.p. 50°-52° C.

The liquid products were purified by chromatography on silica-gel and by distillation in a short path distillation apparatus.

EXAMPLE 5

N,N$^1$-Di-(4-methyl-2-oxazolyl)-1,6-hexanediamine

A solution of 1,6-hexanediamine (11.6 g, 0.10 mol) in tetrahydrofuran (50 ml) was added dropwise to a stirred mixture of cyanogen bromide (21.2 g, 0.20 mol) and sodium carbonate (42.4 g, 0.40 mol) in tetrahydrofuran (75 ml) at −10° to −15° C. The mixture was stirred for 1 hour at this temperature then 1 hour at 0° to 5° C. and 1 hour at 20° to 25° C. Solid was filtered off and the filtrate was evaporated under vacuum without heating to give crude 1,6-hexane dicyanamide as a pale oil (15.3 g).

This cyanamide was dissolved in tetrahydrofuran (20 ml) and water (50 ml) and mixed with a 50% aqueous solution of hydroxyacetone (28.5 g, 0.2 mol). The solution was made strongly basic by addition of 2 N NaOH (40 ml) and was then stirred for 2 hours during which time the title compound crystallised from the solution. Yield 13.6 g, m.p. 124° C.

EXAMPLE 6

N,N$^1$-1,6-hexanediylbis[2-methyl-N(4-methyl-2-oxazolyl)propanamide]

A solution of N,N$^1$-di(4-methyl-2-oxazolyl)-1,6-hexanediamine prepared as described in Example 5 (6.95 g, 0.025 mol) and isobutyric anhydride (8.3 ml, 0.050 mol) in toluene (75 ml) was heated under reflux for 3 hours, cooled, washed successively with dilute HCl, sodium carbonate and sodium chloride solutions, dried and evaporated. The crude product was distilled under vacuum (0.2 mm) in a short path distillation apparatus (air bath temperature 190° C.).

Yield 7.4 g.

Analysis—C: 62.96; H: 7.97; N: 13.19. $C_{22}H_{34}N_4O_4$ requires—C: 63.13; H: 8.19; N: 13.39%.

EXAMPLE 7

N,N$^1$-1,6-hexanediylbis[N-(4-methyl-2-oxazolyl)pentanamide

The title compound was prepared by the method described in Example 6, b.p. 200° C./0.1 mm.

We claim:

1. A compound of the formula:

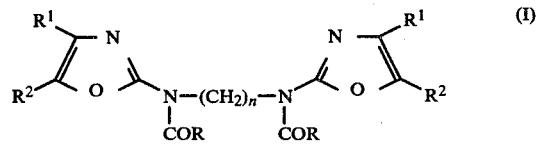

where R is $C_{2-6}$ alkyl, $R^1$ and $R^2$ are hydrogen or $C_{1-4}$ alkyl and n is 3 to 6.

2. A pharmaceutical formulation useful in the treatment of asthma which comprises a compound of claim 1 associated with a pharmaceutically acceptable carrier therefor.

3. A method of prophylactic treatment of a mammal susceptible to asthmatic attack which comprises administering to said mammal a chemotherapeutically-effective amount of a compound of claim 1.

4. The compound of claim 1 wherein $R^1$ is $C_{1-3}$ alkyl and $R^2$ is hydrogen.

5. The compound of claim 4, said compound being N,N$^1$-1,4-butanediylbis[2-methyl-N-(4-methyl-2-oxazolyl)-propanamide].

6. The compound of claim 4, said compound being N,N$^1$-1,3-propanediylbis[2-methyl-N-(4-methyl-2-oxazolyl)-propanamide].

7. The compound of claim 4, said compound being N,N$^1$-1,5-pentanediylbis[2-methyl-N-(4-methyl-2-oxazolyl)-propanamide].

8. The compound of claim 4, said compound being N,N$^1$-1,4-butanediylbis[N-(4-methyl-2-oxazolyl)-pentanamide].

9. The compound of claim 4, said compound being N,N$^1$-1,6-hexanediylbis[2-methyl-N-(4-methyl-2-oxazolyl)-propanamide].

10. The compound of claim 7, said compound being N,N¹-1,6-hexanediylbis[N-(4-methyl-2-oxazolyl)-pentanamide].

11. The formulation according to claim 2 wherein the active agent is a compound of the formula

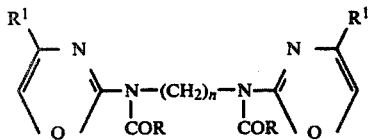

wherein R is $C_{2-6}$ alkyl, $R^1$ is $C_{1-3}$ alkyl and n is 3 to 6.

12. The method of treatment according to claim 3 wherein the active agent administered is a compound of the formula

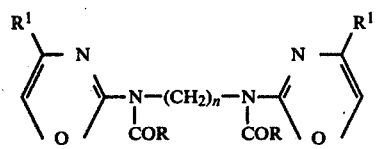

wherein R is $C_{2-6}$ alkyl, $R^1$ is $C_{1-3}$ alkyl and n is 3 to 6.

* * * * *